US010514343B2

(12) United States Patent
Thompson et al.

(10) Patent No.: US 10,514,343 B2
(45) Date of Patent: Dec. 24, 2019

(54) X-RAY CT MICROSCOPY SYSTEM AND METHOD UTILIZING LATTICE SAMPLING

(71) Applicant: Carl Zeiss X-ray Microscopy, Inc., Pleasanton, CA (US)

(72) Inventors: William Thompson, Livermore, CA (US); Zhifeng Huang, Pleasanton, CA (US)

(73) Assignee: CARL ZEISS X-RAY MICROSCOPY, INC., Pleasanton, CA (US)

( * ) Notice: Subject to any disclaimer, the term of this patent is extended or adjusted under 35 U.S.C. 154(b) by 716 days.

(21) Appl. No.: 15/054,194

(22) Filed: Feb. 26, 2016

(65) Prior Publication Data

US 2016/0252467 A1 Sep. 1, 2016

Related U.S. Application Data

(60) Provisional application No. 62/126,195, filed on Feb. 27, 2015.

(51) Int. Cl.
*G01N 23/046* (2018.01)
(52) U.S. Cl.
CPC .................. *G01N 23/046* (2013.01)
(58) Field of Classification Search
CPC ....... A61B 6/508; A61B 6/548; A61B 6/4405; A61B 6/14; A61B 6/505; A61B 6/4411;
(Continued)

(56) References Cited

U.S. PATENT DOCUMENTS 5,740,224 A * 4/1998 Muller ................... G01N 23/04
378/11
7,443,953 B1 10/2008 Yun et al.
(Continued)

FOREIGN PATENT DOCUMENTS

WO 2013184103 A1 12/2013

OTHER PUBLICATIONS

Feldkamp, L.A. et al., "Practical cone-beam algorithm," Journal of Optical Society of America, vol. 1, No. 6, Jun. 1984. Eight pages.
(Continued)

*Primary Examiner* — Irakli Kiknadze
(74) *Attorney, Agent, or Firm* — HoustonHogle LLP (57) ABSTRACT

X-ray microscopy tomography scanning systems are not constrained by continuous scanning trajectories like in medical scanners. In fact, the source and detector can be held stationary during subsequent image capture producing a discrete sampling pattern. For such systems, a method of producing an optimized, even illumination of the object by choosing source/detector locations on a surface of an imaginary cylinder surrounding the object is disclosed. The locations, in one example, form a regular lattice with even coverage on the surface of that cylinder, rather than at locations along a continuous curve such as a helix. Using this method, the effective pitch may be increased beyond the theoretical limit imposed by helical scanning, allowing a greater range of y-axis coverage for the same number of projection angles, corresponding to an increase in throughput.

22 Claims, 7 Drawing Sheets

(58) Field of Classification Search
CPC .......... A61B 6/482; A61B 6/487; A61B 6/54; A61B 6/56; A61B 6/107; A61B 6/462; A61B 6/4441; A61B 6/4452; A61B 6/4482; A61B 6/507; A61B 6/145; A61B 6/542; A61B 6/027; A61B 6/032; A61B 6/583; A61B 6/4028; A61B 6/4007; A61B 6/4085; A61B 6/4275; A61B 6/00; A61B 6/4092; A61B 6/4291; A61B 6/484; A61B 90/36; A61B 2017/00057; A61B 2034/101; A61B 2034/102; A61B 2034/105; A61B 2090/364; G05B 19/401; G01B 11/272; G01B 7/023; G01L 37/023; G01J 3/02; G01J 3/0291; G01J 5/08; G01J 5/0803; G01J 5/0831; G01J 5/0859; G01J 5/089; G01J 5/0896; G01T 1/1611; G01T 1/1615; G01T 1/1648; G01T 1/166; G01T 1/17; G01T 1/175; G01T 1/20; G01T 1/29; G01T 1/2985; G06T 11/005; G06T 2211/432; G01N 23/04; G01N 23/046; G01N 23/2204; G01N 21/658; H05G 1/52; H01J 2237/2807; H01J 37/222
USPC .............................. 378/4, 19, 20, 43, 83–88
See application file for complete search history.

(56) References Cited

U.S. PATENT DOCUMENTS

| | | | | |
|---|---|---|---|---|
| 8,135,186 | B2* | 3/2012 | Bouman | G06T 11/006 378/19 |
| 9,046,465 | B2 | 6/2015 | Thompson et al. | |
| 2004/0071363 | A1* | 4/2004 | Kouri | G06K 9/00516 382/276 |
| 2012/0219116 | A1* | 8/2012 | Thompson | G01N 23/04 378/62 |
| 2017/0052264 | A1* | 2/2017 | Kingston | G01N 23/046 |

OTHER PUBLICATIONS

Fessler, J.A. et al., "Statistical image reconstruction methods for transmission tomography," Handbook of Medical Imaging, Medical Image Processing and Analysis, vol. 2, pp. 1-70, 2000, SPIE. Seventy pages.

Kak, A., et al., "Algebraic Reconstruction Algorithms," Chapter 7 of Principles of Computerized Tomographic Imaging, 1988, IEEE, New Jersey. Twenty-two pages.

Kalender, W., "Technical Foundations of Spiral CT," Seminars in Ultrasound, CT, and MRI, vol. 15, No. 2. Apr. 1994; pp. 81-89. Nine pages.

Katsevich, A., "An improved exact filtered backprojection algorithm for spiral computed tomography," Advances in Applied Mathematics 32 (2004) pp. 681-697. Seventeen pages.

Katsevich, A., "Analysis of an exact inversion algorithm for spiral cone-beam CT," Physics in Medicine and Biology, 17 (2002) pp. 2583-2597. Sixteen pages.

Katsevich, A., "Theoretically Exact Filtered Backprojection-Type Inversion Algorithm for Spiral CT," SIAM Journal of Applied Mathematics, vol. 62, No. 6, pp. 2012-2026, 2002. Fifteen pages.

Noo, F. et al., "Cone-beam reconstruction from general discrete vertex sets," 1996, Nuclear Science Symposium 1996 Conference Record, 1996 IEEE, pp. 1496-1500. Five pages.

Noo, F. et al., "Cone-beam Reconstruction from General Discrete Vertex Sets using Radon Rebinning Algorithms," IEEE Transactions on Nuclear Science, vol. 44, No. 3, Jun. 1997, pp. 1309-1316. Eight pages.

Pack, J. et al., "Investigation of saddle trajectories for cardiac CT imaging in cone-beam geometry," Physics in Medicine and Biology 49 (2004) pp. 2317-2336. Twenty-one pages.

Sidky, E.Y. et al., "Image reconstruction in circular cone-beam computed tomography by constrained, total-variation minimization," Physics in Medicine and Biology 53 (2008) pp. 4777-4807. Thirty-two pages.

Thompson, W. et al., "Optimisation of the Source Firing Pattern for Real Time Cone-Beam Tomography," Proceedings of the 11th International Meeting on Fully Three-Dimensional Image Reconstruction in Radiology and Nuclear Medicine, Jul. 11-15, 2011, pp. 335-338. Four pages.

Thompson, W. et al., "Reduction of Periodic Artefacts for a Switched-Source X-ray CT Machine by Optimising the Source Firing Pattern," Proceedings of the 12th International Meeting on Fully Three-Dimensional Reconstruction in Radiology and Nuclear Medicine, Jun. 2013, pp. 345-348. Four pages.

Thompson, W., Source Firing Patterns and Reconstruction Algorithms for a Switched Source, Offset Detector CT Machine, PhD Thesis, University of Manchester, England, 2011. One hundred eighty-two pages.

Tuy, H., "An Inversion Formula for Cone-Beam Reconstruction," SIAM Journal of Applied Mathematics, vol. 43, No. 3, Jun. 1983. Seven pages.

* cited by examiner

X-RAY CT MICROSCOPY SYSTEM AND METHOD UTILIZING LATTICE SAMPLING

RELATED APPLICATIONS

This application claims the benefit under 35 USC 119(e) of U.S. Provisional Application No. 62/126,195, filed on Feb. 27, 2015, which is incorporated herein by reference in its entirety.

BACKGROUND OF THE INVENTION

X-ray computed tomography (CT) is a non-destructive technique for inspecting and analyzing internal structures of objects. In general, x-rays are absorbed or scattered as the x-rays travel through the objects. The x-rays not absorbed or scattered away are then detected by a detector system. The image formed at the detector system is known as an x-ray projection. Tomographic volume data sets are then reconstructed from a series of these projections as the objects are scanned at different angles via standard CT reconstruction algorithms.

For most X-ray CT microscopy tasks, the preferred source would be a synchrotron. These devices can produce bright, monochromatic, and collimated beams of radiation. Generally, such beam characteristics are ideal for CT microscopy. Synchrotrons are expensive and access to hemlines is often limited, however.

On the other hand, laboratory sources are more common and are lower in cost. Unfortunately, such sources produce beams that are cone-shaped, less bright and have relatively broadband spectral emissions, which include Bremsstrahlung background and characteristic emission lines. Moreover, there is usually a tradeoff between beam brightness and collimation.

SUMMARY OF THE INVENTION

X-ray CT microscopy systems often employ circular scan patterns. This technique has flaws, however. Because of the cone-shaped beams from laboratory x-ray sources, the information collected in the projections is not sufficient to reconstruct the object exactly and artifacts can be present in the reconstruction. Especially for large cone angles, defined as the angle subtended by the detector in the plane orthogonal to the axial plane, severe cone beam artifacts may be observed.

When scanning objects that are long using multiple circular scans, it is therefore necessary to keep the cone angle small to avoid artifacts, which has a negative effect on throughput since small cone angles mean that less x-ray photon flux is accepted by the detector from the source.

Due to the drawbacks associated with circular scan cone beam CT, various alternative scanning trajectories, such as saddle and helical, have been devised, which effectively eliminate the artifacts. In particular the helical scanning trajectory has found widespread use, as it also gives an efficient way of scanning long objects in non-microscopy systems.

The problem with helical scanning is that although this method offers theoretically exact reconstruction, illumination of the object with x-rays is highly uneven. The throughput is limited by the pitch of the helix, where the pitch is defined as the relative translation in the y-axis direction per 360 degree turn (theta). If the maximum allowable pitch is exceeded then the uneven illumination results in regions of the volume receiving less than the necessary 180 degree range of illumination angles, producing severe artifacts. There is also a drop-off in the range of illumination angles in regions toward the ends of the trajectory that result in part of the scanned volume that cannot be reconstructed without artifacts.

X-ray microscopy scanning systems are not constrained by continuous source motion. In fact, the sources and detectors are stationary and the object is moved in the beam. For such systems, the proposed invention can provide a solution of producing an optimized, even illumination of the object by choosing source/detector locations.

If the source/detector locations are characterized as points on a surface of an imaginary cylinder surrounding the object, then the locations are selected to improve the evenness of illumination. In one example, the locations form a regular lattice pattern on the surface of that cylinder, rather than at locations along a continuous curve such as a helix, as in the past. Using this solution, the effective pitch may be increased beyond the theoretical limit imposed by helical scanning, allowing a greater range of y-axis coverage for the same number of projection angles, corresponding to an increase in performance, such as in throughput.

With this method, there also need not be a drop-off in the range of illumination angles towards the ends of the scan range in y, only a gradual sparsifying effect, allowing a potentially larger reconstructed region.

In general, according to one aspect, the invention features a method for sampling an object in an x-ray microscopy system. This method comprises obtaining projections of an object at sampling points by irradiating the object with the x-ray beam and detecting the x-ray beam after passing through the object and rotating the object around a rotation axis that is orthogonal to an optical axis of the x-ray beam and translating the object along the rotation axis between projections so that the sampling points form a two dimensional regular or irregular lattice pattern on an imaginary cylinder surrounding the object.

Preferably, the sampling points of the lattice pattern are spaced to maximize a distance between the sampling points with respect to each other for a fixed number of sampling points per unit area. For example, the sampling points of the lattice pattern are spaced so that distances between any sampling point and its 4, 5 or 6 nearest neighbors are approximately equal or differ by no greater than 50%.

In embodiments, the lattice pattern is hexagonal. Other patterns can be used, however, such as rhombic, square, rectangular, or parallelogrammic. The lattice pattern can even be random or pseudo random.

In some cases, the lattice can be distorted having a higher density of sampling points in the directions in which the object is elongated or has weaker transmission.

In general, according to another aspect, the invention features an X-ray CT microscopy system. The system comprises an x-ray source for generating an x-ray beam, a detector system for detecting the x-ray beam after transmission through an object, and an object stage for holding the object in the x-ray beam and rotating the object around a rotation axis and translating the object along the rotation axis. A computer system controls the object stage to rotate the object and translate the object to access sampling points arranged in a two dimensional regular or irregular lattice pattern on an imaginary cylinder surrounding the object.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, it will be understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Figure 1:
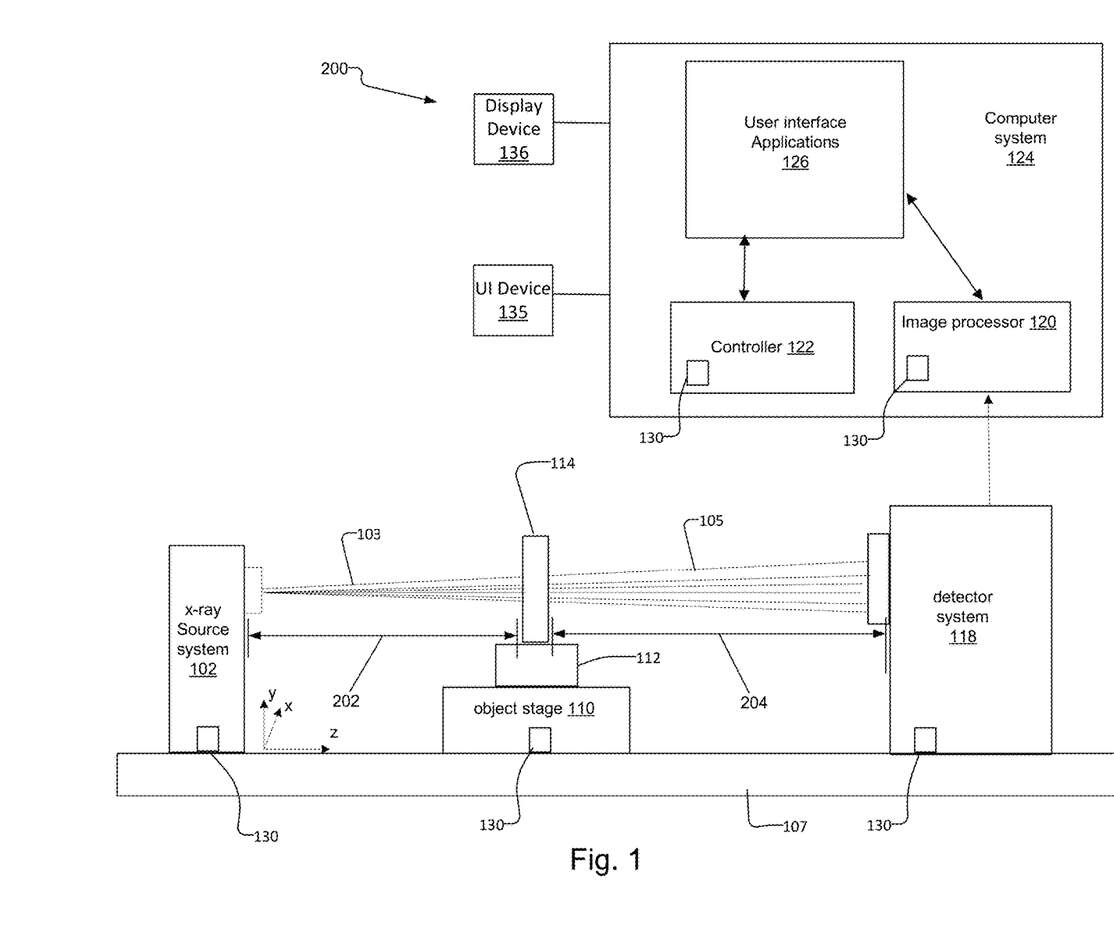
FIG. 1 is a schematic diagram of an X-ray CT microscopy system to which the present invention is applicable.

FIG. 1 is a schematic diagram of an X-ray CT microscopy system 200 to which the present invention is applicable.

The X-ray CT system 200 generally includes an X-ray imaging system that has an X-ray source system 102 that generates a polychromatic or possibly monochromatic X-ray beam 103 and an object stage 110 with object holder 112 for holding the object 114 and positioning it to enable scanning of the object 114 in the stationary beam 103, 105.

The operation of the system 200 and the scanning of the object is controlled by a computer system 124 that often includes an image processor 120, a controller 122, and user interface applications 126 that execute on the computer system. A display device 136 connected to the computer system 124 displays information from the X-ray CT microscopy system 200 such as the tomographic reconstructions. User input device(s) 135 such as a touch screen, computer mouse, and/or keyboard enable interaction between the operator and the computer system 124.

The controller 122. has a controller interface 130 that allows an operator via the computer system 124 to control and manage components in the X-ray CT system 200 under software control via the computer system 124.

The source 102 is a synchrotron x-ray radiation source or alternatively a "laboratory x-ray source", in some embodiments. As used herein, a "laboratory x-ray source" is any suitable source of x-rays that is not a synchrotron x-ray radiation source.

Laboratory x-ray source 102 can be an X-ray tube, in which electrons are accelerated in a vacuum by an electric field and shot into a target piece of metal, with x-rays being emitted as the electrons decelerate in the metal. Typically, such sources produce a continuous spectrum of background x-rays combined with sharp peaks in intensity at certain energies that derive from the characteristic lines of the selected target, depending on the type of metal target used. Furthermore, the x-ray beams are divergent and lack spatial and temporal coherence.

In one example, source 102 is a rotating anode type or microfocused source, with a Tungsten target. Targets that include Molybdenum, Gold, Platinum, Silver or Copper also can be employed. Preferably a transmission configuration is used in which the electron beam strikes the thin target from its backside. The x-rays emitted from the other side of the target are used as the beam 103.

In another, more specific example, source 102 is a structured anode x-ray source such as described in U.S. Pat. No. 7,443,953 issued to Yun, et al. on Oct. 28, 2008, the contents of which are incorporated herein by reference in their entirety. In this case, the source has a thin top layer made of the desired target material and a thicker bottom layer made of low atomic number and low density materials with good thermal properties. The anode can include, for instance, a layer of copper with an optimal thickness deposited on a layer of beryllium or diamond substrate.

X-ray lasers producing radiation having an energy suitable for the tomographic applications described herein also can be employed.

In still another example, the source 102 is a metal jet x-ray source such as are available from Excillum AB, Kista, Sweden. This type of source uses microfocus tubes in which the anode is a liquid-metal jet. Thus, the anode is continuously regenerated and already molten.

The x-ray beam 103 generated by source 102 is preferably conditioned to suppress unwanted energies or wavelengths of radiation. For example, undesired wavelengths present in the beam are eliminated or attenuated, using, for instance, an energy filter (designed to select a desired x-ray wavelength range (bandwidth)).

The beam extent is preferably reduced by passing the x-ray beam through an aperture device, having a beam defining pinhole or appropriate square aperture. This aperture limits the illuminated region on the object 114 and restricts the size of the direct beam on the x-ray detection system 118.

When the object 114 is exposed to the X-ray beam 103, the X-ray photons transmitted through the object form an attenuated x-ray beam 105 that is received by the detector system 118. In some other examples, the objective lens is used to form an image onto detector system 118 of the X-ray system.

Typically, a magnified projection image of the object 114 is formed on the detector system 118. The magnification is equal to the inverse ratio of the source-to-object distance 202 and the source-to-detector distance 204. To achieve high resolution, the X-ray CT system 200 utilizes a very high resolution detector system 118 in conjunction possibly with positioning the object 114 close to the X-ray source system 102. In this case, the resolution of the x-ray image is limited by the resolution of the detector system 118, the focus spot size of the X-ray source system 102, the position of the object 114 and the geometrical magnification of the object 114 at the detector system 118.

For adjusting the geometrical magnification, the operator utilizes the user interface applications 126 on the computer system 124 to adjust the source-to-object distance 202 and the source-to-detector distance 204. The operator adjusts these distances to achieve the desired geometrical magnification. In typical examples, the geometrical magnification is often greater than 2 or 4 or possibly 8. In some cases, the geometrical magnification is greater than 100.

The operator or the system under automatic control operates the object stage 110 to perform the CT scan via the controller 122 and the control interfaces 130 between the controller 122 and the object stage 110. Typically, the object stage will position the object by rotating the object about an axis that is orthogonal to the optical axis of the x-ray beam 103, 105. Typically, theta rotation is utilized in which the object 114 is rotated about the y-axis, which is orthogonal to the surface of the optical table or platform 107 of the system 200. The object stage further moves or translates the object 114 in the y-axis direction.

The detector system 118 creates an image representation, in pixels, of the X-ray photons from the attenuated X-ray beam 105 that interact often with a scintillator in the detector system 118. The image formed at the detector system 118 is also known as a projection or projection image.

Using the user interface applications 126, the operator defines/selects CT scan parameters. These include X-ray voltage settings associated with the X-ray energy spectrum of the scan and exposure time on the X-ray source system 102. The operator also typically selects other settings such as the field of view of the X-ray beam 103 incident upon the object 114, the number of X-ray projection images to create for the object 114, and the angles to rotate and position the object stage 110 to rotate the object and position the object along the y-axis in order to implement lattice sampling of the object 114 for an X-ray CT scan in the stationary X-ray beam 103.

The computer system 124, with the assistance of its image processor 120, accepts the set of images from the detector system 118 associated with each rotation angle/y-axis position of the object 114. The image processor 120 combines the projection images using a CT reconstruction algorithm to create 3D tomographic volume information for the object. The reconstruction algorithm may be analytical, where convolution or frequency domain filtering of the projection data is combined with back projection onto a reconstruction grid. Alternatively, it may be iterative, where techniques from numerical linear algebra or optimization theory are used to solve a discretized version of the projection process, which may include modeling of the physical properties of the imaging system.

The source trajectory of an x-ray CT system refers to the path along which the x-ray source moves relative to the object being scanned. Since the X-ray CT microscopy system 200 employs a fixed source and typically requires longer exposure times, the object position relative to the source beam at each exposure is taken to represent a discrete sampling point in 3D space.

In X-ray microscopy CT systems, the source and detector positions are fixed during the scan, and the object is manipulated on the object rotation stage 110. This is equivalent by a simple transformation into coordinate systems having the convention that the source and detector are moved around the object, which we are adopting here. Assuming that the source to object distance remains constant during the scan, then the set of all possible source positions is a cylinder surrounding the object, with radius equal to the source to rotation center distance. Analogous to the source trajectory in continuous motion CT, the distribution of source positions forms a discrete sampling pattern on the surface of the cylinder.

Figure 2:
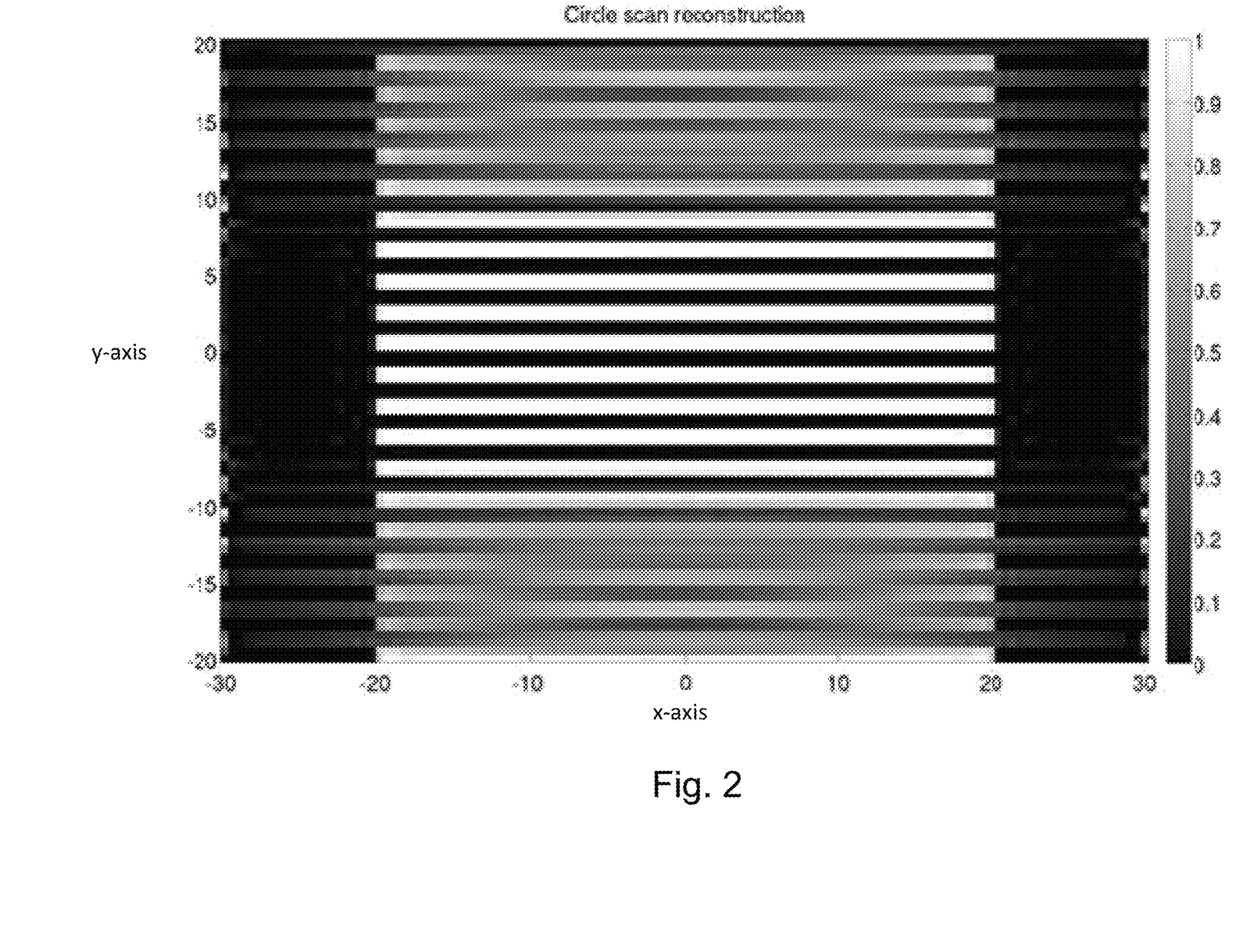
FIG. 2 is a coronal/sagittal plane cross sectional view of a reconstruction of a phantom from a circular CT scan.

FIG. 2 is a coronal/sagittal plane cross sectional view of a reconstruction from a circular CT scan of a phantom consisting of discs. The reconstruction was made using the FDK algorithm (see L. A. Feldkamp, L. C. Davis and J. W. Kress. Practical cone-beam algorithm, *J. Opt. Soc. Am. A.* 1(6):612-619, 1984), which represents the standard, state-of-the-art analytical technique for reconstruction of such datasets. The plane of the discs is chosen to be parallel to the central axial slice of the tomography. Cone beam artifacts associated with large cone angle circular scan reconstruction appear for the discs farther away from the central axial plane.

To address these artifacts, other scanning trajectories have been employed.

Figure 3A:
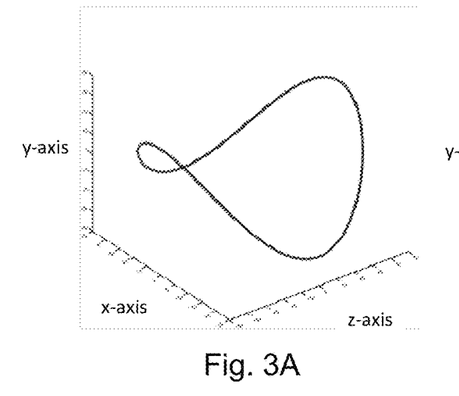
FIGS. 3A and 3B illustrate a saddle and helical CT scanning trajectories.
Figure 3B:
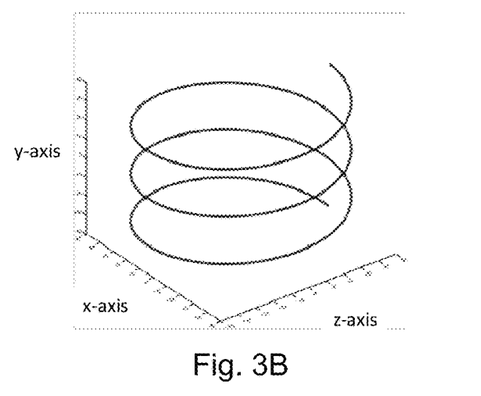

For example, FIGS. 3A and 3B illustrate a saddle and helical CT scanning trajectories. Object translation is in the y-axis direction.

Lattice Sampling

The present invention concerns lattice sampling. This refers to the case when the sampling pattern forms an irregular pattern or a regular pattern such as a hexagonal one (see FIG. 4). Other regular lattice patterns can be used such as rhombic, square, rectangular, and/or parallelogrammic. In irregular lattice patterns, the sampling points have pseudo random and random spatial distributions over the imaginary cylinder surrounding the object.

Figure 4:
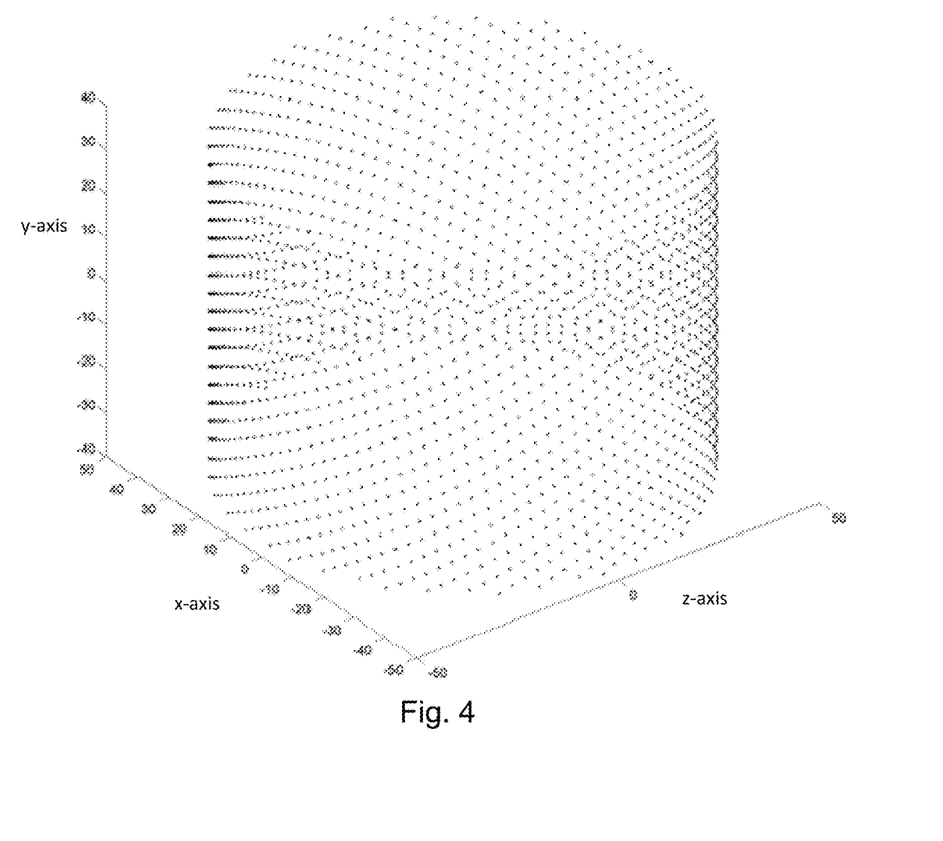
FIG. 4 shows an example of a regular lattice sampling pattern for an X-ray CT microscopy system according to the present invention, the source/detector locations being characterized as points on a surface of an imaginary cylinder surrounding the object.

These different patterns of sampling points can be used so long as the placement of points facilitates the more even distribution of the points over the surface. These various patterns and rules spread the source positions out as evenly as possible, and gives an even illumination of the object 114.

In operation, the controller 122 of the computer system 124 controls the object stage 110 via the control interface 130 to rotate the object 114 and translate the object 114 along the y-axis so that one of the sampling points on the imaginary cylinder surrounding the object (see FIG. 4) is aligned with the optical axis of the beam 103, 105 from the source 102.

Once aligned, the controller 122 via the control interface 130 then activates the x-ray source system 102 to irradiate the object 114. The controller then reads-out the two dimensional projection image captured by the pixilated detector of the detector system 118.

Once the projection has been stored by the computer system 124, the controller 122 instructs the object stage 110 to rotate the object and/or translate the object along the y-axis to access the next sampling point of the lattice on the imaginary cylinder.

This process repeats until projections from all of the intended sampling points have been captured and stored by the computer system 124.

Once all of the sampling points of the lattice on the imaginary cylinder have been accessed and the corresponding projections obtained by the computer system 124, then the computer system performs tomographic reconstruction of the object 114 based on the projections.

In cases where the source and detector to object distances do not remain constant throughout the scan, the set of possible source positions relative to the object forms a more general two-dimensional surface around the object. For example, if the source to object distance is varied smoothly between two values then this will form a cylinder with an elliptical profile. In these cases, a lattice sampling pattern is defined in the same way.

Figure 5:
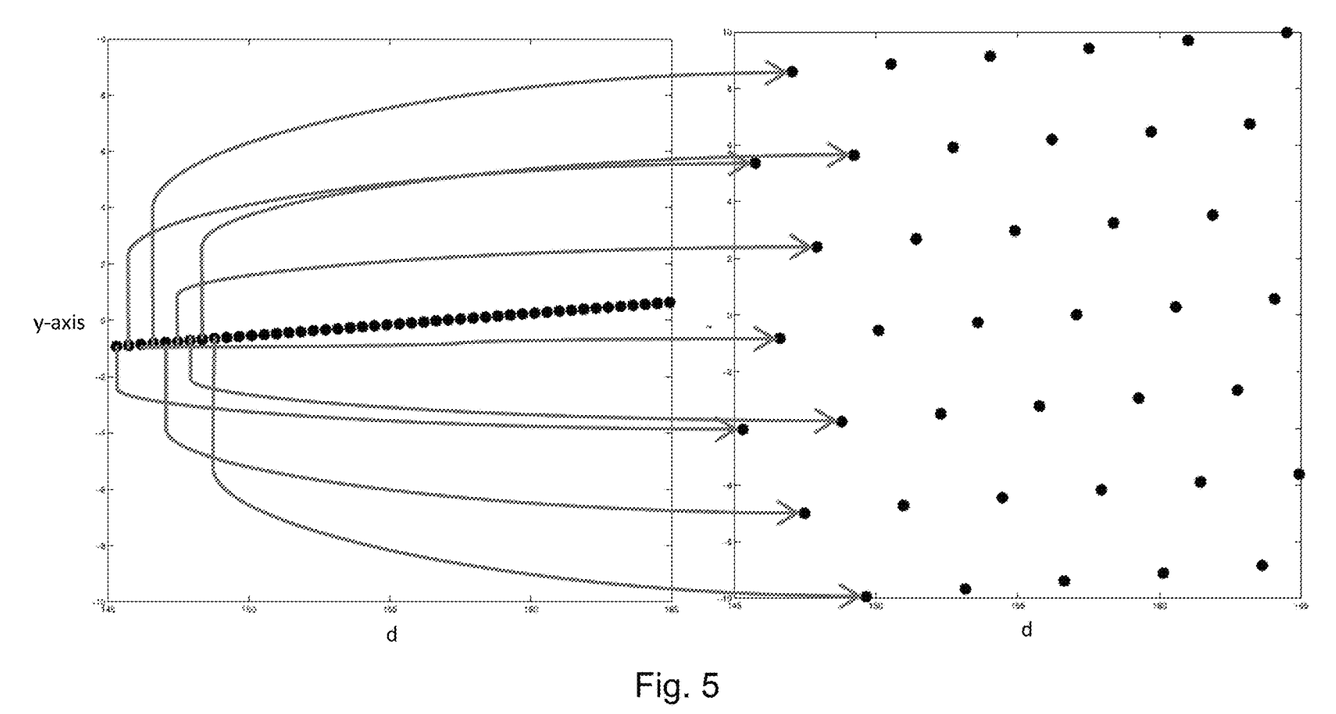
FIG. 5 illustrates a regular lattice sampling pattern as a permutation of the discretized helical scan.

The discretely sampled helical source trajectory relative to the object gives a densely sampled pattern of points lying on a straight line, leaving large areas of the cylinder with no sampling points. The redistribution of sampling points from a helical scan pattern into lattice sampling pattern is shown in FIG. 5, illustrating the more even distribution of points obtained with lattice sampling. The diagrams show a section of the surface of the cylinder of possible source points, peeled away and flattened. The horizontal axis represents distance (d) along the cylinder's circumference.

Figure 6A:
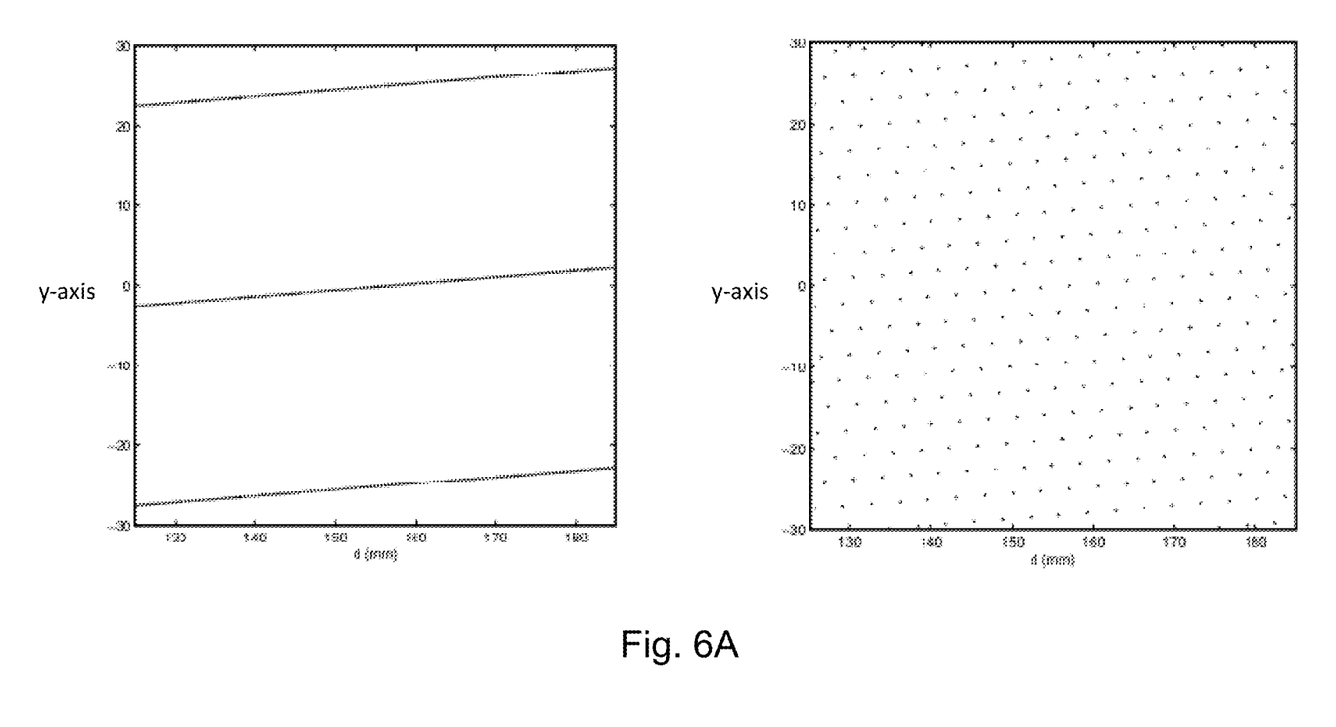
FIG. 6A is a comparison of surface coverage for helical scanning (left) and a regular lattice sampling pattern (right) for the same number of points. The plots show a section of the surface of the cylinder of possible source points, peeled away and flattened. The horizontal axis represents distance (d) along the cylinder's circumference.

FIG. 6A is a comparison of surface coverage for helical scanning (left) and lattice sampling (right). The number of sampling points is the same for both methods, but the coverage is much better for the lattice sampling case.

Figure 6B:
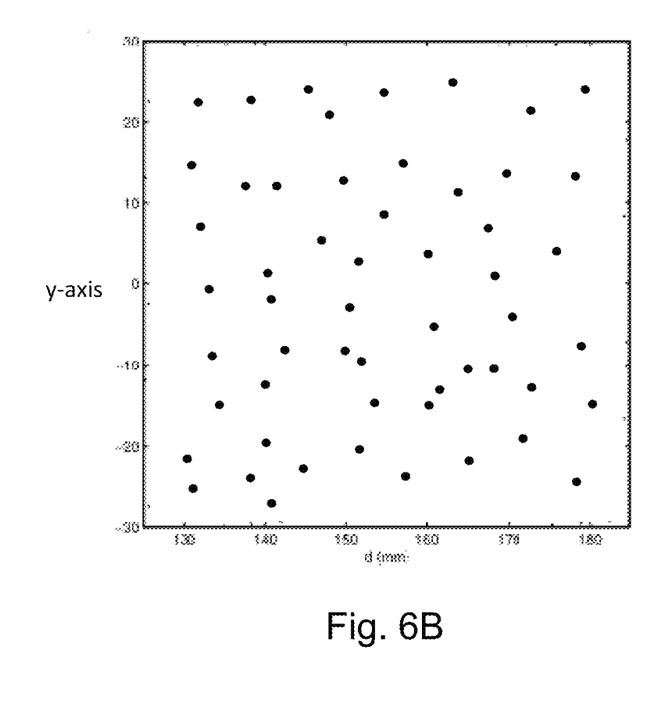
FIG. 6B shows an irregular (random) lattice sampling pattern on a section of the surface of the cylinder of possible source points, peeled away and flattened. The horizontal axis represents distance (d) along the cylinder's circumference.

FIG. 6B shows an irregular (random) lattice sampling pattern on a section of the surface of the imaginary cylinder of possible source points, peeled away and flattened. Here also, the horizontal axis represents distance (d) along the cylinder's circumference.

In order to specify a lattice sampling pattern, first define a coordinate system on the surface of an imaginary cylinder, representing the set of possible source positions, as (d, y), where d is the distance along the circumference of the cylinder, and y is the position in the vertical direction. The value of d lies in the range [0, 2πR), where R is the cylinder's radius, and y can take any real value. Values of d are defined to wrap around modulo 2πR.

Define an open disk on the surface of the cylinder, centered at $(d_0, y_0)$ and of radius r, as the set $$\{(d,y) | (d-d_0)^2 + (y-y_0)^2 < r^2\}.$$

This is simply the area of the cylinder's surface covered by the disk, up to its boundary.

Define a sampling pattern of points on the surface of the cylinder, and assume that this can be periodically extended infinitely in the y-axis direction. These points represent the source positions around an arbitrarily long object. Now define $r_{min}$ as the minimum value of r such that every open disk of radius $r_{min}$ contains at least one sampling point, for all possible values of $d_0$ and $y_0$. In other words, if you take a disk of radius $r_{min}$ and move it over the surface of the cylinder, it will always contain at least one sampling point.

The value of $r_{min}$ quantifies the evenness of the lattice's surface coverage; lower values indicate a more even, and possibly also denser distribution. For a given sampling density, defined as the number of sampling points within a finite range of y values, the distribution which minimizes $r_{min}$ gives the most even coverage.

Consider any lattice sampling pattern that is regular or periodic; i.e. not a collection of randomly located points, and ignore the special case of a square or rectangular grid. For any point in the lattice, define its neighbors as the six closest points, such that a straight line from each neighbor to the point does not pass through any other points on the lattice. The value of $r_{min}$ is given by the radius of the circle which circumscribes the triangle formed by the lines connecting a point and its two furthest neighbors. Intuitively, one can see that in order to minimize $r_{min}$, these three points should be located at equal angles around this circle's circumference, at a spacing of 120 degrees. This creates a regular hexagonal lattice; therefore, for maximum evenness, the sampling pattern should be chosen to be as close to a regular hexagonal lattice as possible. In order to achieve this, the distances between neighboring points, as defined above, should be chosen to be as close to equal as possible, ideally.

On the other hand, the sampling points of the lattice, whether regular or irregular, should not be spaced so that distances between any sampling point and its 4, 5 or 6 nearest neighbors differs by greater than 50%. Preferably, the sampling points of the lattice are spaced so that distances between any sampling point and its 4, 5 or 6 nearest neighbors differs less than 10%.

The lattice sampling pattern can be generated from a discretized helical scan by a mathematical permutation of the y positions, as shown in FIG. 5. In the simplest case, projections are assumed to be taken at equally spaced angles. For the discretized helical scan, the y position at the $i^{th}$ projection angle is given by $$y_i = i\delta_y,$$

where $\delta_y$ is the y vertical translation (pitch) divided by the number of projections per helical turn. For the lattice sampling pattern, the y position at the $i^{th}$ projection angle is given by $$y_i = [(k(i-1) \bmod N) + 1]\delta_y,$$

where N is the number of projections per full rotation, and k is some integer coprime to N. For an appropriate value of k, this generates an even lattice with the property that the source y positions are evenly distributed across each full source rotation.

The lattice construction parameter k can be determined empirically by calculating the lattice patterns for each candidate value of k, and minimizing the standard deviation of the distances between points. Since the lattice produced by the equation above is rotationally symmetrical, it is only necessary to consider a single point and, for the hexagonal case, the distances to its six nearest neighbors. The optimal value of k depends on the number of projections per full source rotation, the y translation per full rotation (pitch) and the source to rotation center distance.

The well-known classical analytical reconstruction algorithms for CT are all derived from the concept of a continuous scanning trajectory, and as such cannot be applied directly in the case of lattice sampling.

On the other hand, algebraic iterative algorithms, see A. C. Kak and M. Slaney. *Principles of Computerized Tomographic Imaging*, IEEE Service Center, Piscataway, N.J., 1988, chapter 7, based on numerical solution of a discretized representation of the projection process are not dependent on scanning method and can therefore be used for reconstruction of lattice scans without modification. Iterative algorithms based on total variation (TV) minimization (see E. Y. Sidky and X. Pan, Image reconstruction in circular cone-beam computed tomography by constrained, total-variation minimization. *Phys. Med. Biol.*, 53(17):4777-4807, 2008) have the capability to produce low noise reconstructed images from sparsely sampled data while preserving edges. Similarly, in statistical iterative algorithms, including those incorporating edge-preserving regularization (see J. A. Fessler, M. Sonka and J. M. Fitzpatrick, Statistical image reconstruction methods for transmission tomography, *Handbook of Medical Imaging, Medical Image Processing and Analysis*, vol. 2, pp. 1-70, 2000, SPIE) the reconstruction process is formulated as an optimization problem including accurate physics and noise modeling. These are also not dependent on scanning method and may be used without modification. These algorithms can be used by the computer system 124 to increase scanning throughput by using a more sparsely sampled lattice with increased pitch. Note that this would be impossible to achieve using helical scanning since increasing the pitch leads to unrecoverable systematic errors caused by an inadequate range of illumination angles for certain regions of the reconstruction volume.

In one embodiment, an approximate analytical filtered back projection algorithm based on a modification of the circular scan cone beam algorithm of Feldkamp, Davis and Kress (FDK), see L. A. Feldkamp, L. C. Davis and J. W. Kress. Practical cone-beam algorithm, *J. Opt. Soc. Am. A*, 1(6):612-619, 1984, is employed by the computer system 124. Using this method, some artifacts may be present in the reconstructed images; however, the output of the modified FDK algorithm can then be used as the seed for an algebraic or statistical iterative reconstruction algorithm providing a fast and accurate hybrid reconstruction method. This may also be combined with methods employing TV minimization, or other edge-preserving regularization techniques in the case of a sparsely sampled lattice in order to improve convergence speed and reduce the total time to results.

Forming the lattice using the procedure described in connection with some embodiments above results in a sampling pattern that is rotationally and translationally symmetric; the lattice pattern as viewed from the perspective of a source point is the same regardless of the source point chosen. This symmetry can be exploited to simplify the computational cost of the reconstruction algorithm. If the reconstruction volume is set up so that the transaxial (x-z) slices coincide with the y values of the lattice points, then the projection matrix is effectively the same for each slice. The coefficients representing volume contributions for each ray may therefore be stored for only one slice, and reused for all other slices. The resulting reconstructed volume consists of a stack of rotated slices, each rotated by a constant angle, which depends on the lattice parameters used. The slices can then be rotated back into the correct alignment after the reconstruction process.

The proposed method solves the problem of systematic artifacts in circular scan cone beam CT by providing a method of illuminating the object from source points evenly distributed on the surface of a cylinder. This fulfills the criterion for obtaining an exact reconstruction using an alternative continuum model of the scanning process.

Figure 7:
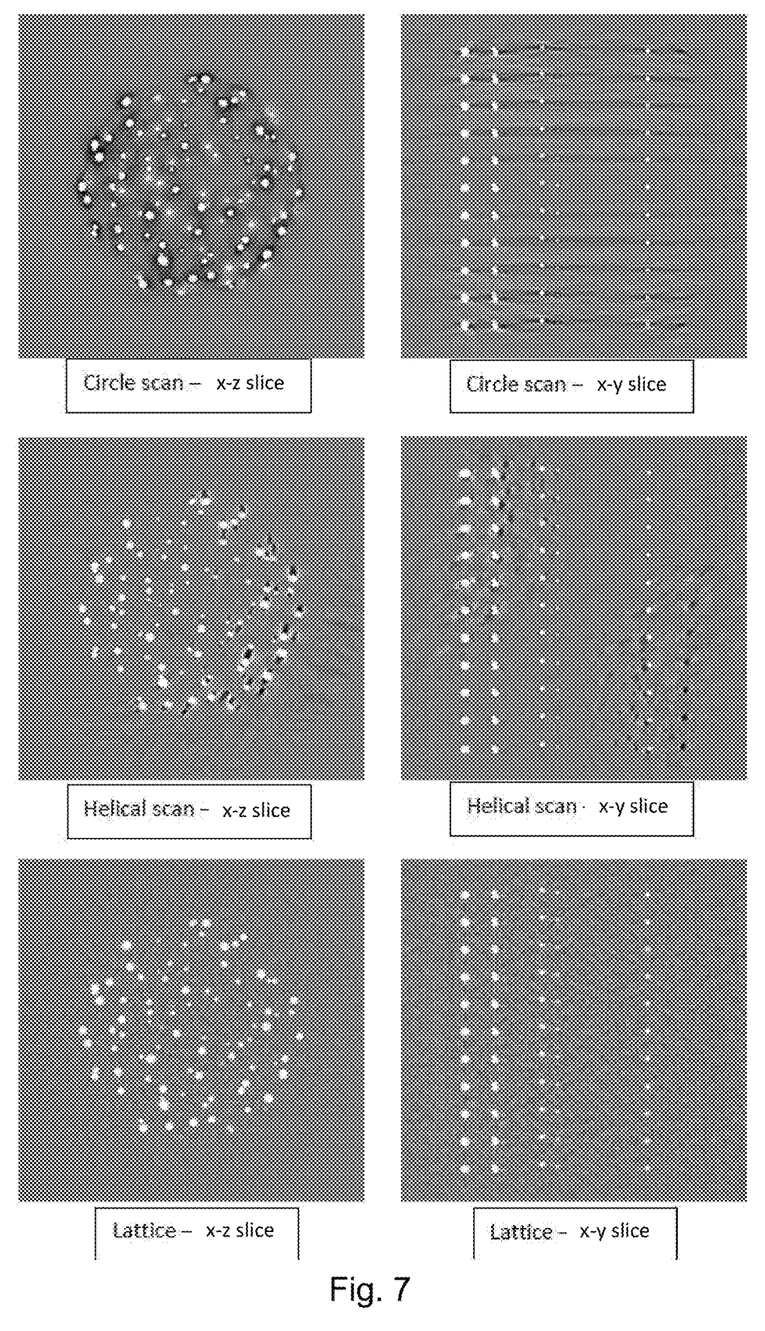
FIG. 7 includes a series of images that enable comparison of reconstructed simulated data for circle, helical and lattice scans. The simulated object consists of a number of planes of small spheres, each plane aligned to the central transaxial slice and offset by a fixed amount. Transaxial slices are shown on the left, coronal/sagittal on the right. Note strong cone beam artifacts in circle scan case and strong limited angle artifacts in helical scan case.

FIG. 7 gives an example of reconstruction of simulated data sets taken with circular, helical and lattice scans, demonstrating complete elimination of the artifacts using the proposed invention.

Compared to helical scanning, the proposed method provides a more even illumination of the object, resulting in higher achievable pitch and therefore throughput. It also avoids the problem of uneven illumination of sample points in a helical scan which can lead to non-isotropic image quality throughout the reconstruction volume for large cone angles, as demonstrated in FIG. 7. A technique similar to the described lattice tomography is described in W. M. Thompson, W. R. B. Lionheart and E. J. Morton. Optimization of the source firing pattern for x-ray scanning systems, U.S. Pat. No. 9,046,465 B2, applying to CT systems with multiple discrete sources. However, in this case, the optimization of the lattice is based on the specific case where the pitch is small, and the generated lattice contains only two rows of points per unit pitch. In contrast, the present method and system considers optimization of the lattice in its full generality, and is applicable to a wider range of system geometries such as those with a stationary beam and moving object. The present approach preferably uses an evenly-spaced lattice of source sampling points in order to create an even illumination of the reconstruction volume from the full range of projection angles, and from a full range of y positions.

Generating the lattice from a permutation of the discretized helical scanning trajectory provides rotational symmetry. The rotational symmetry simplifies calculation of an optimal lattice and may also lead to design of more efficient reconstruction algorithms. It is also possible to vary the pattern and density of the sampling points slightly to be non-uniform within some range without affecting the performance significantly.

Other lattice patterns could be used in other embodiments and achieve equivalent results. In general, lattice coverage can be chosen that is not strictly symmetric but still has a dense pattern. The pattern could even be random or pseudo random so long as the coverage is relatively even. One could also imagine a distorted lattice which has a higher density of sampling points in the directions the object is elongated or has a weaker transmission. This would be done to optimize the signal collected and provide an optimum fidelity reconstruction.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for sampling an object in an x-ray microscopy system, comprising:
    obtaining projections of an object at sampling points by irradiating the object with an x-ray beam and detecting the x-ray beam after passing through the object; and
    rotating the object around a rotation axis that is orthogonal to an optical axis of the x-ray beam and translating the object along the rotation axis between projections so that the sampling points form a two dimensional lattice pattern on an imaginary cylinder surrounding the object; and
    wherein the sampling points of the lattice pattern are spaced so that distances between any sampling point and its 4, 5 or 6 nearest neighbors are approximately equal or differ by no greater than 50%.

2. A method as claimed in claim 1, wherein the sampling points of the lattice pattern are spaced to maximize a distance between the sampling points with respect to each other for a fixed number of sampling points per unit area.

3. A method as claimed in claim 1, wherein the lattice pattern is hexagonal.

4. A method as claimed in claim 1, wherein the lattice pattern is a hexagonal pattern with quasi-equidistant spacing.

5. A method as claimed in claim 1, wherein the lattice pattern is rhombic, square, rectangular, or parallelogrammic.

6. A method as claimed in claim 1, wherein the lattice pattern is random or pseudo random.

7. A method as claimed in claim 1, comprising a single x-ray source and a pixelated two dimensional detector system for detecting the x-rays from the x-ray source.

8. A method as claimed in claim 1, wherein the lattice is rotationally and translationally symmetric.

9. A method as claimed in claim 1, wherein the lattice pattern as viewed from the perspective of a source point is the same regardless of the source point chosen.

10. A method as claimed in claim 1, wherein the lattice is distorted having a higher density of sampling points in the directions in which the object is elongated or has weaker transmission.

11. An X-ray CT microscopy system, comprising:
an x-ray source for generating an x-ray beam;
a detector system for detecting the x-ray beam after transmission through an object;
an object stage for holding the object in the x-ray beam and rotating the object around a rotation axis and translating the object along rotation axis; and
a computer system controls the object stage to rotate the object and translate the object to access sampling points arranged in a two dimensional lattice pattern on an imaginary cylinder surrounding the object, wherein the sampling points of the lattice pattern are spaced so that distances between any sampling point and its 4, 5 or 6 nearest neighbors are approximately equal or differ by no greater than 50%.

12. A system as claimed in claim 11, wherein a computer system activates the x-ray source to irradiate the object and the computer system reads out two dimensional projection images captured by the detector system for the sampling points of the lattice pattern.

13. A system as claimed in claim 12, wherein tomographic reconstruction of the object is performed based on the projection images.

14. A system as claimed in claim 11, wherein the sampling points of the lattice pattern are spaced to maximize a distance between the sampling points with respect to each other for a fixed number of sampling points per unit area.

15. A system as claimed in claim 11, wherein the lattice pattern is hexagonal.

16. A system as claimed in claim 11, wherein the lattice pattern is a hexagonal pattern with quasi-equidistant spacing.

17. A system as claimed in claim 11, wherein the lattice pattern is rhombic, square, rectangular, or parallelogrammic.

18. A system as claimed in claim 2, wherein the lattice pattern is random or pseudo random.

19. A system as claimed in claim 11, wherein the lattice pattern is rotationally and translationally symmetric.

20. A system as claimed in claim 11, wherein the lattice pattern as viewed from the perspective of a source point is the same regardless of the source point chosen.

21. A system as claimed in claim 11, wherein the lattice is distorted having a higher density of sampling points in the directions the object is elongated or has weaker transmission.

22. A computed tomography system, comprising:
an x-ray beam source for generating an x-ray beam;
an x-ray detector system for detecting the x-ray beam after transmission through an object;
an object stage for holding the object in the beam and rotating the object around a rotation axis and translating the object along the rotation axis; and
a computer system controls the object stage to rotate the object and translate the object to access sampling points arranged in a two dimensional lattice pattern on an imaginary cylinder surrounding the object, wherein the computer system reads out two dimensional projection images captured by, the detector system for the sampling points of the lattice pattern to perform tomographic reconstruction of the object based on the projection images, wherein the sampling points of the lattice pattern are spaced so that distances between any sampling point and its 4, 5 or 6 nearest neighbors are approximately equal or differ by no greater than 50%.

* * * * *

UNITED STATES PATENT AND TRADEMARK OFFICE
CERTIFICATE OF CORRECTION

PATENT NO. : 10,514,343 B2  
APPLICATION NO. : 15/054194  
DATED : December 24, 2019  
INVENTOR(S) : William Thompson and Zhifeng Huang Page 1 of 1

It is certified that error appears in the above-identified patent and that said Letters Patent is hereby corrected as shown below:

In the Claims

Claim 11, Column 11, Line 32, delete "translating the object along rotation axis; and" and insert --translating the object along the rotation axis; and--;

Claim 18, Column 12, Line 15, delete "A system as claimed in claim 2, wherein the lattice" and insert --A system as claimed in claim 11, wherein the lattice--;

Claim 22, Column 23, Line 38, delete "images captured by, the detector system for the sam-" and insert --images captured by the detector system for the sam- --.

Signed and Sealed this  
Twenty-fifth Day of February, 2020

Andrei Iancu  
*Director of the United States Patent and Trademark Office*